(12) United States Patent
Ellard et al.

(10) Patent No.: US 6,179,262 B1
(45) Date of Patent: Jan. 30, 2001

(54) STABILIZER ASSEMBLY FOR STEPPER APPARATUS AND ULTRASOUND PROBE

(75) Inventors: Terence R. Ellard, Seattle; Stephen Knudsen, Bainbridge Island, both of WA (US)

(73) Assignee: Real World Design & Development Co., Seattle, WA (US)

( * ) Notice: Under 35 U.S.C. 154(b), the term of this patent shall be extended for 0 days.

(21) Appl. No.: 09/178,440

(22) Filed: Oct. 23, 1998

(51) Int. Cl.$^7$ .................................................. E04G 3/00
(52) U.S. Cl. ..................................... 248/276.1; 248/278.1
(58) Field of Search .............................. 248/278.1, 276.1, 248/280.11, 274.1, 282.1, 288.5

(56) References Cited

U.S. PATENT DOCUMENTS

| | | | | |
|---|---|---|---|---|
| 1,382,783 | * | 6/1921 | Howard | 248/278.1 |
| 4,795,118 | * | 1/1989 | Kosugi et al. | 248/288.5 |
| 5,104,103 | * | 4/1992 | Auchinleck et al. | 248/276.1 |
| 5,118,058 | * | 6/1992 | Richter | 248/278.1 |
| 5,842,672 | * | 12/1998 | Sweere et al. | 248/278.1 |
| 5,961,527 | * | 10/1999 | Whitmore, III et al. | 606/130 |

OTHER PUBLICATIONS

"The Brachystand" and "Brachystepper" product brochure Barzell–Whitmore Maroon Bells, Inc.

* cited by examiner

Primary Examiner—Anita M. King
Assistant Examiner—Jerome DeLuca

(57) ABSTRACT

The stabilizer assembly is used to position a stepper assembly for an ultrasound probe. The stabilizer includes two spaced apart swivel assemblies, each swivel assembly including clamps at one end thereof locking the stabilizer to a table. Each swivel assembly includes several swivel arms which are connected at three spaced swivel points. One swivel arm is connected to a central assembly consisting of a central housing with two spaced apart ball joints connecting, respectively, to the two swivel assemblies. A linkage arrangement maintains the ball joints in a locked position by virtue of a spring biased push rod. To unlock the ball joints, the spring is compressed by actuation of a trigger, releasing pressure on the linkage assembly which permits the ball joints to move freely.

30 Claims, 3 Drawing Sheets

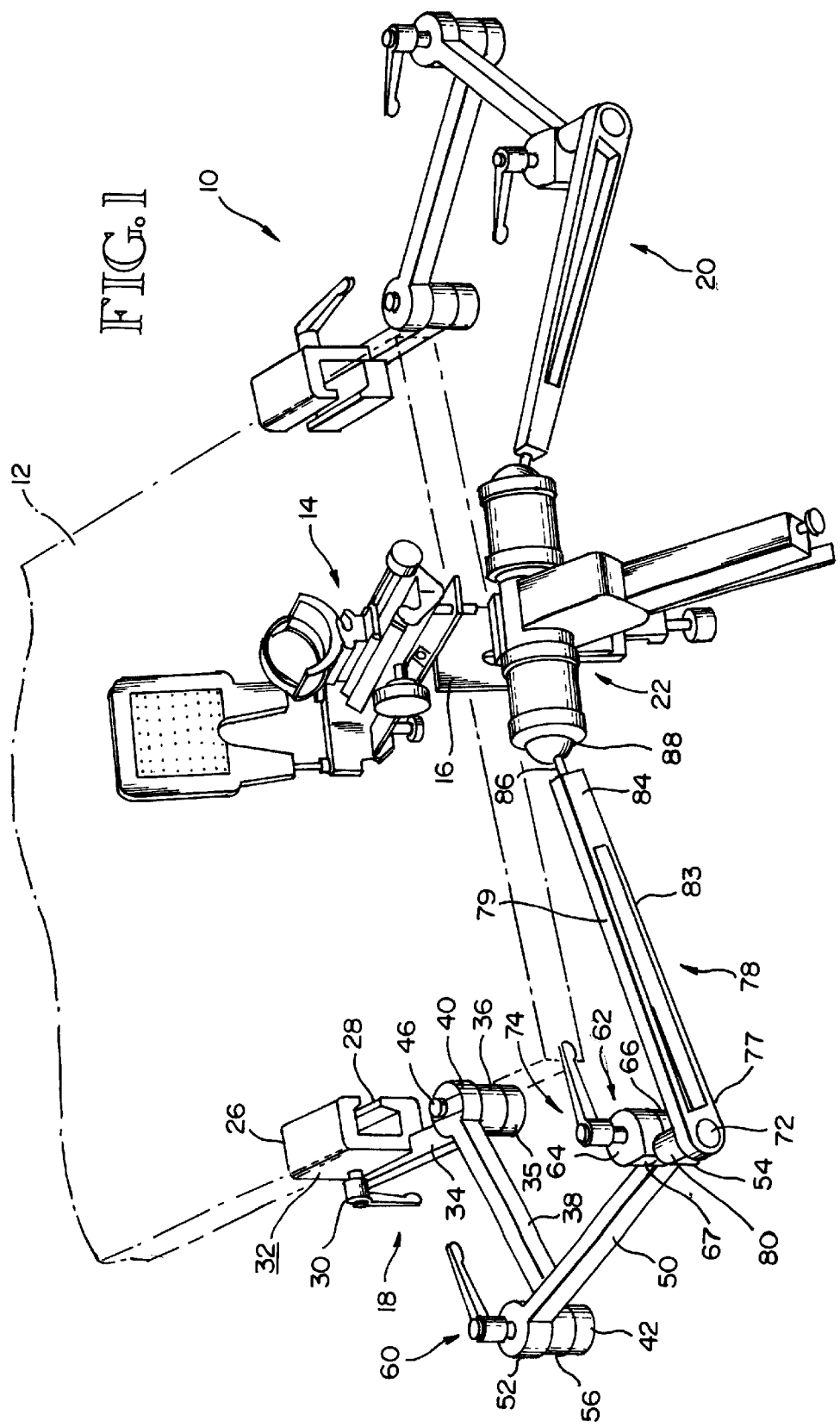

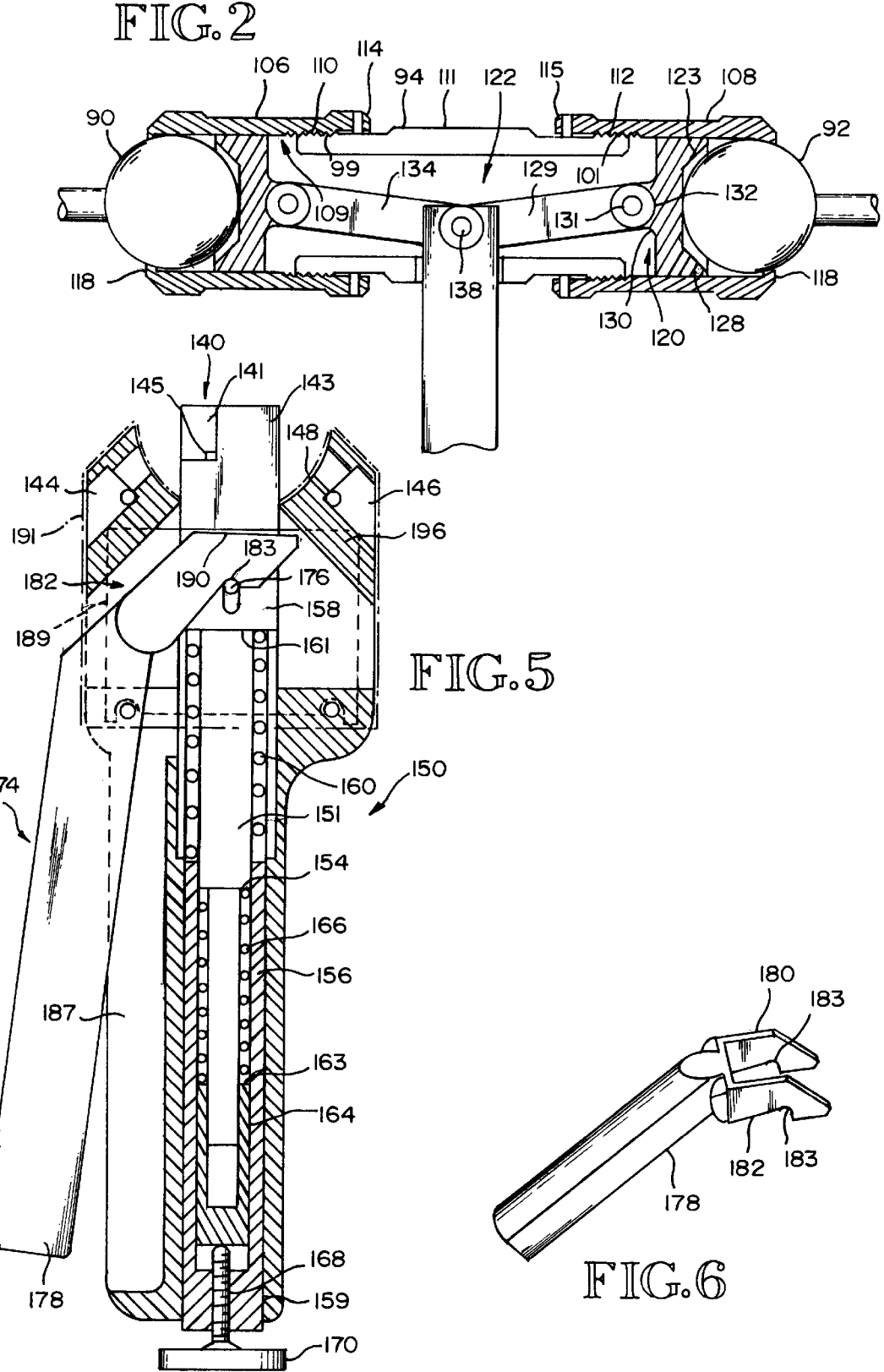

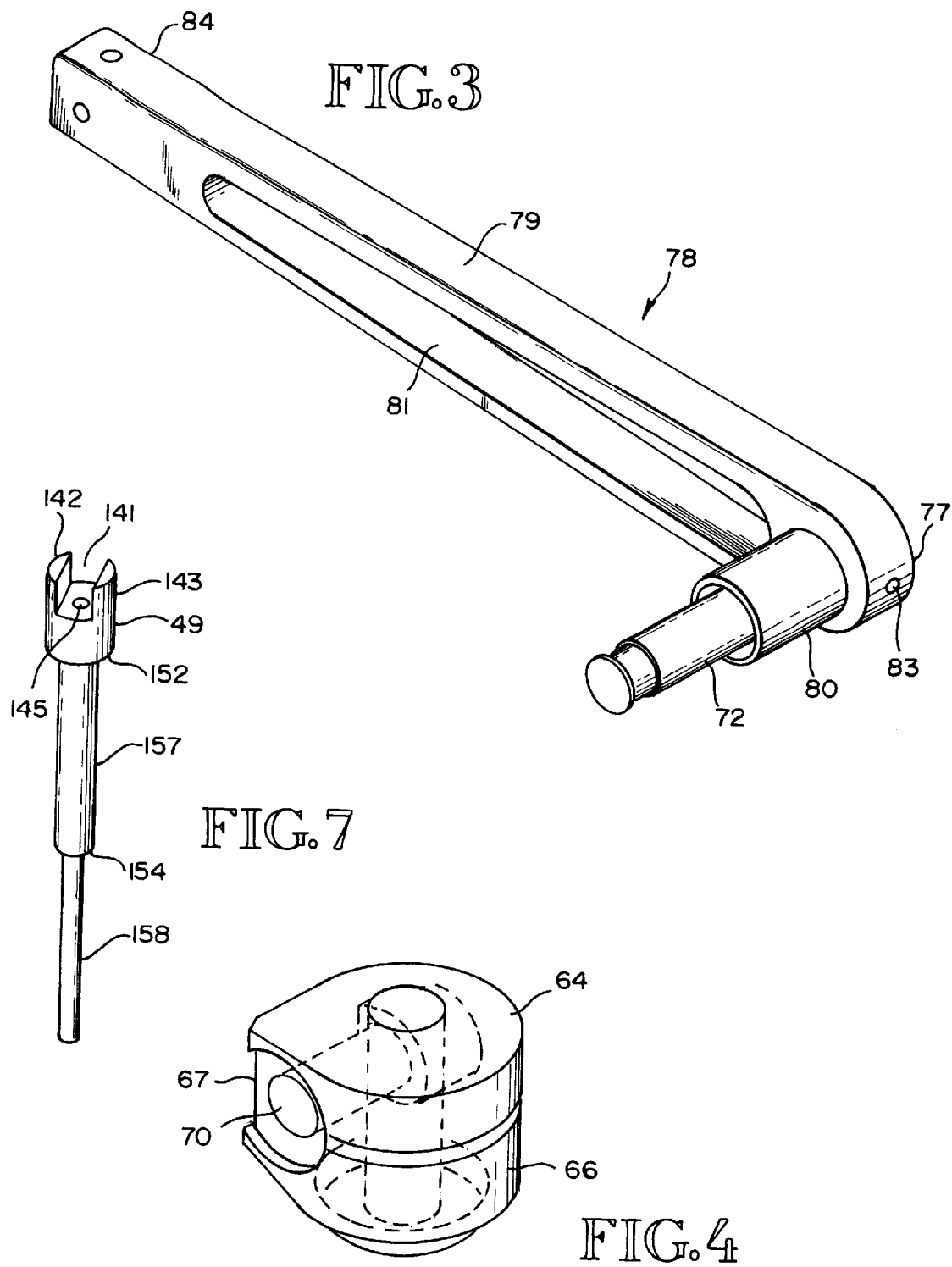

STABILIZER ASSEMBLY FOR STEPPER APPARATUS AND ULTRASOUND PROBE

TECHNICAL FIELD

This invention relates generally to stabilizer assemblies, and more particularly concerns such an assembly used to support a stepper apparatus and ultrasound probe, wherein the stabilizer assembly is designed to permit convenient movement of the stepper apparatus, in multiple degrees of freedom.

BACKGROUND OF THE INVENTION

Many types of apparatus require a mounting fixture, referred to herein as a stabilizer, to accurately position the apparatus. The stabilizer can then be locked in a desired position, from where the apparatus can, if desired, be moved precisely by virtue of an intermediate device such as a stepper assembly.

One example of such a stepper assembly supported by a stabilizer is shown in pending U.S. patent application Ser. No. 08/949,731. As disclosed in that application, an ultrasound probe, supported by the stepper apparatus, is used in the treatment of prostate cancer by a procedure known as brachytherapy, in which radioactive seeds are accurately positioned at selected locations within the prostate. Effective brachytherapy requires a precise initial positioning of the ultrasound probe relative to the patient by means of a stabilizer assembly, locking the stabilizer in position and then moving the ultrasound probe by a stepper assembly in precise selected increments in order to accurately position the radioactive seeds at preselected locations in the prostate.

The combination of a stepper apparatus and ultrasound probe is, however, only one example of use of a stabilizer assembly. Various devices can be mounted on a stabilizer assembly for use in a variety of applications.

Stabilizer assemblies can take various forms, although they all must be supported from a fixed mounting structure. In an operating room environment, such as for brachytherapy, the stabilizer assembly is supported from the floor or from the operating table on which the patient is positioned.

Known stabilizer assemblies, including those used to support the combination of a stepper apparatus and an ultrasound probe, are typically difficult to manipulate by the physician, are often cumbersome and unreliable in operation and are susceptible to jamming. This is often frustrating and disconcerting for the physician. In addition, reliable and convenient locking of the stabilizer in a particular position is often difficult, and the range and variety of movement possible for many stabilizers is not satisfactory.

Hence, a new stabilizer is desirable which is reliable and convenient to operate, readily lockable in a desired position, easily attachable to a variety of mounting structures, and in particular is capable of moving smoothly and precisely, into virtually any position desired by the physician.

SUMMARY OF THE INVENTION

Accordingly, the present invention is a stabilizer assembly for supporting a medical instrument such as a combination of a stepper apparatus and ultrasound probe, comprising: two spaced-apart swivel assemblies, each swivel assembly including at least one swivel connection permitting movement of a portion of the swivel assembly in a horizontal plane and at least one other swivel connection permitting movement of a portion of the swivel assembly in a vertical plane, and further including means for locking the swivel connections; a central head assembly, including a housing and at least one universal joint, the central head assembly including means locking the universal joint and means connecting the universal joint to the swivel assemblies, respectively; and handle means extending from the central head assembly which includes means for unlocking the universal joint to permit movement of the central head portion.

BRIEF DESCRIPTION OF THE DRAWINGS

FIG. 1 is a perspective view showing the complete stabilizer assembly of the present invention.

FIG. 2 is a cross-sectional diagram showing a central head portion of the assembly of FIG. 1.

FIG. 3 is a perspective view of a particular arm portion of the stabilizer assembly of FIG. 1.

FIG. 4 is a perspective, transparent view of a joint portion of the stabilizer assembly of FIG. 1.

FIG. 5 is a cross-sectional diagram showing a handle portion of the assembly of FIG. 1.

FIG. 6 is a perspective view of a push rod used in the central head portion of FIG. 4 and the handle portion of FIG. 5.

FIG. 7 is a perspective view of a trigger portion of the handle of FIG. 5.

BEST MODE FOR CARRYING OUT THE INVENTION

FIG. 1 shows the stabilizer assembly of the present invention, generally referred to at 10, mounted on an operating table 12 upon which the patient is positioned for brachytherapy treatment of prostate cancer. As discussed above, however, the stabilizer can be used to accurately support and position other devices, particularly medical devices which require precise positioning and reliable locking. Stabilizer assembly 10 is shown supporting a stepper apparatus, shown generally at 14, which is positioned on a mounting plate 16 which in turn is secured to the stabilizer assembly. Stepper apparatus 14 of FIG. 1 supports an ultrasound probe (not shown) used in brachytherapy. Stepper apparatus 14 in FIG. 1 is disclosed in detail, as indicated above, in the '731 co-pending application. Stepper apparatus 14 and its use in brachytherapy is not part of the present invention but is used to illustrate one application as well as the operation of the stabilizer assembly 10.

Stabilizer assembly 10 includes left and right side sections 18 and 20 and a central head section 22. The left and right side sections are substantially identical, being mirror images of each other. The left side section 18 will be described in detail herein; it should be understood that such description is applicable to the right side section 20. Left side section 18 includes a rail clamp 26 which secures stabilizer assembly 10 to operating table 12. Clamp 26 is generally C-shaped, with a narrow opening 28 through which a rail at the edge of the table is inserted. A first locking element and ratchet arm 30 extends through a side surface 32 of clamp 26, bearing against the edge of the table rail, holding clamp 26 firmly thereagainst. The locking element and ratchet arm 30 are conventional and are therefore not described in detail. The ratchet arm portion thereof is arranged such that turning (ratcheting) the arm in one direction increases the locking pressure; the arm will turn freely in the other direction, while the locking pressure holds, to a convenient position from where the locking pressure can be further increased by again ratcheting the arm in the one direction.

A rail arm 34 is attached to rail clamp 26 by means of screws or the like and extends forwardly from the rail clamp. Rail arm 34 is in the embodiment shown approximately 7.75 inches long, approximately 0.75 inches thick and approximately 0.75 inches wide. At the distal end of rail arm 34 is a circular portion 35 having a diameter of 1.5 inches with an opening through the center thereof. A circular spacer 36 is positioned on top of circular portion 35. A first swivel arm 38 is connected to and extends from the circular portion of rail arm 34, forming a first swivel connection. The first swivel arm 38 in the embodiment shown is approximately 9.5 inches long, 0.75 inches wide, and includes circular portions 40 and 42 at the proximal and distal ends respectively.

Circular portion 40 at the proximal end is positioned on top of spacer 36. Circular section 40 of swivel arm 38, circular section 35 of rail arm 34 and spacer 36 are secured together by a pin 46. First swivel arm 38 and the rail arm 34 are free to rotate horizontally relative to each other about pin 46. The arrangement of the first swivel connection, including the spacer 36 and the pin 46 are conventional and are therefore not described in detail.

A second swivel arm 50 is identical to the first swivel arm 38. Second swivel arm 50 has circular sections 52 and 54 at proximal and distal ends thereof. Circular section 52 is positioned in registry with circular section 42 of first swivel arm 38. A spacer 56 is positioned between circular section 42 of swivel arm 38 and circular section 52 of second swivel arm 50, as seen from bottom to top. A second locking element and ratchet arm 60 extends through the three elements, locking them together by ratcheting the arm portion. This forms the second swivel connection. When ratchet arm 60 is released, the first and second swivel arms are free to rotate horizontally about the locking element portion.

The second swivel arm 50 extends to a vertical joint 62, which is shown most clearly in FIG. 4. Vertical joint 62 comprises upper and lower portions 64 and 66 which are joined together at one side edge 67 thereof, leaving a slight separation between portions 64 and 66. Upper portion 64 can be forced slightly downwardly under pressure toward lower portion 66. Circular section 52 at the distal end of the second swivel arm is secured to the bottom surface of vertical joint 62. Vertical joint 62 is approximately 1.75 inches high and is approximately 1.6 inches in diameter.

Extending horizontally through vertical joint 62 near the one edge 67 thereof at mid-height is a cylindrical opening, the diameter of which extends equally into the upper and lower portions. The opening 70 accommodates a bearing rod 72 (shown in FIG. 3) which extends from an adjacent vertical arm member 78. A locking element and ratchet arm 74 extends down through the upper and lower portions of vertical joint 62, and locks the second swivel arm 50 and the bearing rod 72 in position, preventing rotation of the second swivel arm 50 in the horizontal plane and vertical rotation of bearing rod 72 (and hence vertical arm 78) in cylindrical opening 70.

Bearing rod 72 extends between cylindrical opening 70 and one end 77 of a vertical arm 78. Bearing rod 72 is fixedly connected to one end 77 of vertical arm 78 by means of a screw 83 or the like. Vertical arm 78 in the embodiment shown is approximately 10.6 inches long and has a circular opening at the one end 77 thereof to receive the bearing rod. In the embodiment shown, the vertical arm gradually tapers from a width of 1.3 inches at end 77 approximately 0.75 inches at the other end thereof. Vertical arm 78 is cut out along most of its length leaving upper and lower sections 79 and 81, each approximately 0.15 inches thick.

In the embodiment shown, bearing rod 72 is approximately 3.3 inches long and 0.5 inches in diameter over most of its length. A cylindrical spring sleeve 80 approximately 2.04 inches long and 0.875 inches in diameter, fits over the bearing rod, extending between vertical joint 62 and vertical arm 78. Inside sleeve 80 is a torsion spring (not shown), the ends of which are secured, respectively, to vertical joint 62 and vertical arm 78. The torsion spring provides a small amount (approximately 5 lbs.) of resistance to partially counteract the weight of the stepper assembly and the central head portion.

At the other end 84 of vertical arm 78 is an axial opening to receive a support rod portion 86 of a ball joint 88. Support rod 86 is fixedly attached to end 84 of vertical arm 78 by means of a screw or the like.

In operation each side section can swivel horizontally at the first swivel connection between rail arm 34 and the first swivel arm 38 and the second swivel connection between the first and second swivel arms. The second swivel arm also swivels horizontally about vertical joint 62, the third swivel connection. Vertical arm 78 swivels in a vertical plane about joint 62, through bearing rod 72. Vertical joint 62 and the second swivel connection can be locked, preventing movement of the various arms of the side section about those joints.

FIG. 2 shows the central head portion of the stabilizer system in more detail, including opposing ball joints 90 and 92 located at opposite ends of the central head portion. The central head portion also includes an inner housing member 94 and two spaced outer housing members 106 and 108. Inner housing member is a hollow cylindrical portion approximately 3.75 inches long, with an outside diameter of approximately 1.62 inches and an inner diameter of approximately 1.15 inches. A center section 111 of the inner housing member has a slightly greater exterior diameter. The inner housing member 94 also includes threaded portions 99 and 101, each approximately 0.5 inches wide, at opposing ends thereof.

The outer housing members 106 and 108 are also each generally cylindrical, approximately 2.5 inches long with an exterior greatest diameter of approximately 2 inches and an interior diameter of approximately 1.55 inches. A center portion 113 of the outer housing member has a slightly decreased external diameter. The internal surface 109 of the outer housing members 106 and 108, include threaded sections 110 and 112, respectively, each approximately 0.67 inches wide, beginning at a point approximately 0.33 inches inboard from the inboard ends 114 and 115, respectively, thereof. Outer housing member 106 and 108 can therefore be conveniently threaded onto the respective ends of inner housing member 94.

At the outboard end of each outer housing member is a small inwardly extending lip 118. Lip 118 has a diameter of 1.44 inches, slightly smaller than the diameter of the ball joints 90 and 92, which have a diameter slightly less than the internal diameter of the outer housing members, but slightly greater than the diameter of the free edge of lip 118.

The ball joints 90 and 92 can move laterally within the outer housing member between the inner housing member and lip 118, unless they are locked. The ball joints are pressed outwardly against lip 118 by a combination of a push element 120 and linkage assembly 122. Push element 120 includes a base portion 128, which has a diameter of approximately 1.5 inches, slightly less than the internal diameter of the outer housing members, so that it slides easily within the outer housing member. The base portion 128 has an angled lip portion 123 around its periphery, extending toward the adjacent ball joint. The base portion 128 of the push element 120 thus extends around a portion of the ball joint against which it bears.

Extending rearwardly from base portion 128 of push element 120 is a connector portion 130 which has an opening 131 therein, to which is rotatably connected a link arm 129 by means of a pin 132. The same is true for the other push element, which bears against the other ball joint. Link arm 129 extends from push element 120 to approximately the center of the inner housing member 94, while opposing link arm 134 extends from the other push element to the center of the inner housing member 94.

Link arm 134 at its center end includes two spaced extending projections with openings therein, while link 129 at its center end includes a single extending projection with an opening therein which is designed to fit between the two projections of link arm 134. The openings in the projections are all in registry. A pin 138 connects the two link arms in a rotating relationship.

A push rod 140 makes contact with the two link arms 129 and 134 at their connected center ends. Pushing up on push rod 140 provides the linkage system with a varying mechanical advantage (depending on the angle of the link arms) as the push elements are forced outwardly against ball joints 90 and 92, which bear against the lips 118 of the outer housing members with sufficient force to lock the ball joints in place against those lips. The push rod 140 is shown in more detail in FIG. 6. The upper end of the push rod is circular, approximately 0.875 inches in diameter. A rectangular cutout portion 141 extends through the upper end of the push rod leaving two opposed ear sections 142, 143. Cutout portion 141 is 0.5 inches wide and 0.47 inches deep. In the bottom surface of cutout portion 141 is a small pad 145. The ear sections 142, 143 extend around the mated center ends of the link arms 129 and 134 and the pad 145 contacts the bottom surface of the center ends.

Push rod 140 extends down through a handle 150, which is shown in detail in FIG. 5 and is connected to the inner housing member 94 by means of two screws (not shown) which extend through opposing openings 144 and 146 at the top of the handle. The handle is approximately 7¾ inches long and approximately 1 inch thick. The top of the handle includes a semicircular cutout portion 148 which fits around a portion of the inner housing member 94 of the central head portion. The upper portion of the handle is approximately 2¼ inches wide and 2.75 inches long. The lower portion of the handle is approximately 5 inches long and 1½ inches wide. Push rod 140 extends down through a cylindrical opening in the handle. An upper portion 149 of the push rod is approximately 1.17 inches high. At the lower end of the upper portion, the push rod decreases in diameter to slightly less than 0.5 inches, defining a first shoulder 152 and an intermediate portion 157. Positioned around the upper end of the intermediate portion 157 and adjacent first shoulder 152 is a collar 153 which has a diameter of 0.875 inches and is approximately 0.75 inches high.

Positioned within the cylindrical opening in the lower portion of the handle is a first support tube 156. Support tube 156 is open at the top end thereof and had a threaded portion 159 at the lower end thereof which mates with a matching threaded portion at the lower end of the handle. Longitudinal portion 157 of the push rod moves up and down within tube 156. A main spring 160 extends between top edge 151 of support tube 156 and the lower edge 161 of collar 153. Main spring 160 maintains an upward pressure on the push rod 140 and thus linkage 122 through collar 153, with linkage 122 maintaining locking pressure on the ball joints 90 and 92. The pressure from main spring 160 can be adjusted by turning tube 156 in one direction or another.

Push rod 140 decreases in diameter again to 0.23 inches, for a length of 2.96 inches, to its lower end, defining a second shoulder 154 and another longitudinal portion 158. A secondary tube 164 is positioned within the first support tube 156 at the lower end thereof. Extending between the top edge 163 of secondary tube 164 and second shoulder 154 is a pretensioning spring 166. The tension on the pretensioning spring can be adjusted by means of a screw 168 which has a turning knob 170. The top of screw 168 extends through the bottom of support tube 156 and bears against the closed bottom surface of secondary tube 164. Turning the knob 170 in one direction will increase the tension of spring 166 while turning the knob in the other direction will decrease the tension. Both pretension spring 166 and main spring 160 urge push rod 140 upwardly against linkage assembly 122 in the central head portion, maintaining ball joints 90 and 92 in a locked position.

The handle 150 also includes a trigger member 174 (shown also in FIG. 7) which is arranged such that when the trigger is pulled toward the body of handle 150, the tension of main spring 160 on push rod 140 is released, which releases the pressure on the linkage 122 to a sufficient extent that the ball joints come unlocked, permitting them to rotate. This is accomplished by the interaction of the trigger with two opposing pins 176 which extend outwardly from collar 153 on opposing sides thereof. As indicated above, collar 153 is positioned on push rod 140, against the first shoulder and extending downwardly therefrom. Main spring 160 abuts the lower edge of the collar.

Referring to FIGS. 5 and 7, trigger 174 includes an elongated portion 178 which in the embodiment shown is approximately 2.5 inches long, ⅝ inches wide and ¾ inches thick. At the top of elongated portion 178 are two spaced wing sections 180 and 182. The wing sections angle away from portion 178 at approximately 30° for a small part, then angle again from the small part at approximately 50°. In the lower surface of the wing sections 180, 182 are small semicircular cutout portions 183 which, respectively, fit over the pins 176 on opposite sides of the collar.

The handle 150 includes a first cutout portion 187 in one side thereof into which the elongated portion 138 will move when the trigger is pulled in the direction of the handle and also includes a second cutout portion 189 which extends completely through the handle at the top of the first cutout portion and into which a portion of the trigger joining the two wing sections to the elongated section fits. The trigger 174 is basically free floating, supported by the two pins 176—176 on opposing sides of the handle. Side cover plates 191 (shown in dash/dotted lines in FIG. 5) are attached to the front and rear surfaces of the handle, closely following the outline of the upper portion of the handle and covering up the wing portions of the trigger and the collar pins 176—176 when in place. The cover plates, which are held in by screws (openings shown in FIG. 5) include a rectangular internal cutout section 189 (outline shown in dotted lines) into which the wing portions fit. The upper edge 190 of each wing portion fits against an upper edge 196 of the cutout portion 189 of its associated cover plate.

When the trigger is actuated by pulling it toward the body of the handle, a part of the upper edge 190 of each wing portion will bear against the internal upper edge 196, acting together in essence as a pivot for the trigger. The pivoting action forces the 176—176 and collar 153 downwardly against the action of main spring 160. This in turn results in push rod 140, with the pressure thereagainst of main spring 160 released, moving downwardly, removing the locking pressure on the ball joints, although the pretensioning spring 166 will still exercise some pressure on push rod 140, so that the ball joints are not completely free floating.

When trigger 174 is not actuated, the ball joints 90, 92 are locked into place by the joint pressure of the main spring 160 and the pretensioning spring 166. However, if the swivel connections in the side assemblies are unlocked, the central head portion is still free to move in and out (horizontally), although not vertically. Further, the central head portion cannot move even if the ball joints are locked, if all of the swivel connections are locked. In operation, the central head portion will be located in a desired position when everything is unlocked. The ball joints are then locked, and adjustments are made to the in/out position of the central head portion. The swivel connections are then all locked, locking the entire assembly in position.

When the ball joints and the swivel connections are unlocked, the central head portion can move in six degrees of freedom. When the ball joints are locked but the swivel connections are not, the central head portion can move in two degrees of freedom.

The advantage of the arrangement shown with its horizontal and vertical swivel points in combination with the central head portion which includes two spaced ball joints, is a considerable freedom of movement with the movement being quite smooth and controlled. The stabilizer apparatus may be easily and reliably locked in any desired position. Once the stabilizer is locked, the stepper apparatus can then be reliably moved incrementally.

Although a preferred embodiment of the invention has been disclosed herein for illustration, it should be understood that various changes, modifications and substitutions may be incorporated in such embodiment without departing from the spirit of the invention which is defined by the claims which follow:

What is claimed is:

1. A stabilizer assembly for supporting a medical instrument, comprising:
   two spaced-apart swivel assemblies, each swivel assembly including at least one swivel connection permitting movement of a portion of the swivel assembly in a horizontal plane and at least one other swivel connection permitting movement of a portion of the swivel assembly in a vertical plane, and further including means for locking the swivel connections;
   a central head assembly, including at least one universal joint, the central head assembly including means for locking the universal joint and means connecting the universal joint to the swivel assemblies respectively; and
   handle means extending from the central head assembly which includes means for unlocking the universal joint to permit movement of the central head assembly, wherein the central head assembly is capable of moving in six degrees of freedom when the swivel assemblies and the universal joint are unlocked and of moving in two degrees of freedom when the universal joint is locked but the swivel assemblies are unlocked.

2. A system of claim 1, wherein the central head assembly includes a housing and two universal joints at opposing ends of the housing, and wherein the universal joints, respectively, are connected to the swivel assemblies.

3. A system of claim 2, including clamping members locking each of the swivel assemblies to a table.

4. A system of claim 3, wherein each swivel assembly includes a support rod which is fixedly connected to the clamping member and extends therefrom to the one swivel connection, a first swivel rod which extends from the first swivel connection to a third swivel connection and a second swivel rod which extends from the third swivel connection to the other swivel connection, wherein the first and second swivel rods rotate in the horizontal plane about the one and third swivel connections, each swivel assembly further including a vertical arm which extends between the other swivel connection and a universal joint in the central head assembly, wherein the vertical arm swivels in a vertical plane about the other swivel connection, wherein the other and third swivel connections include means for locking the vertical arm and the first and second swivel arms in place.

5. A system of claim 4, including a spring element connected between the vertical arm and the other swivel connection which results in a counterbalance effect on the vertical arm to prevent the central head assembly from dropping downwardly when the universal joints are unlocked.

6. A system of claim 2, wherein the unlocking means is in the form of a trigger which when actuated acts to unlock the two spaced universal joints.

7. A system of claim 2, wherein the universal joint locking means includes a linkage assembly and two pusher members, the pusher members contacting a portion of the respective universal joints, tending to force them outwardly against a portion of the central head assembly housing, locking the universal joints in place.

8. A system of claim 7, wherein the universal joints are ball joints and said portion of the housing is a lip at an outboard end of the housing.

9. A system of claim 8, wherein the universal joint locking means further includes a push rod which is urged against the linkage assembly so as to force the pusher members outwardly, the locking means including a main spring which acts against a first portion of the push rod, urging the push rod against the linkage assembly.

10. A system of claim 9, wherein the main spring is supported so as to maintain pressure on the push rod against the linkage and wherein a trigger assembly is arranged to compress the main spring so as to release the spring pressure on the push rod, thereby releasing pressure on the linkage and permitting the ball joints to rotate.

11. A system of claim 9, including means for adjusting the tension of the main spring.

12. A system of claim 9, including a second spring acting on a second portion of the push rod tending to force it against the linkage assembly, wherein the pressure of the second spring provides a small amount of pressure on the ball joints, requiring some effort on the part of the operator to move the ball joints with the handle, such that the central head assembly generally remains in position when the trigger is actuated.

13. A system of claim 12, including means for adjusting the tension of the second spring.

14. A stabilizer assembly, comprising:
   two spaced-apart swivel assemblies, each swivel assembly arranged to permit movement of the swivel assembly in a horizontal plane and a vertical plane and further including means for locking the swivel assembly in position;

a central head assembly which includes at least one universal joint, the central assembly including means for locking the universal joint and means connecting the universal joint to the swivel assemblies, respectively; and handle means extending from the central head assembly which includes means for unlocking the universal joint, wherein the central head assembly is capable of moving in six degrees of freedom when the swivel assemblies and the universal joint are unlocked and of moving in two degrees of freedom when the universal joint is locked but the swivel assemblies are unlocked.

15. A stabilizer assembly for supporting a medical instrument, comprising:

two spaced-apart swivel assemblies, each swivel assembly including at least one swivel connection permitting movement of a portion of the swivel assembly in a horizontal plane and at least one other swivel connection permitting movement of a portion of the swivel assembly in a vertical plane, and further including means for locking the swivel connections;

a central head assembly, which includes two universal joints, the central head assembly including means for locking the universal joints and means connecting the two universal joints, respectively, to the two swivel assemblies; and handle means extending from the central head assembly which includes means for unlocking the two universal joints substantially simultaneously with a single action, to permit movement of the central head assembly.

16. A system of claim 15, including clamping members locking each of the swivel assemblies to a table.

17. A system of claim 16, wherein each swivel assembly includes a support rod which is fixedly connected to the clamping member and extends therefrom to the one swivel connection, a first swivel rod which extends from the first swivel connection to a third swivel connection and a second swivel rod which extends from the third swivel connection to the other swivel connection, wherein the first and second swivel rods rotate in the horizontal plane about the one and third swivel connections, each swivel assembly, respectively, further including a vertical arm which extends between the other swivel connection and one of the universal joints in the central head assembly, wherein the vertical arm swivels in a vertical plane about the other swivel connection, wherein the other and third swivel connections include means for locking the vertical arm and the first and second swivel arms in place.

18. A system of claim 17, including a spring element connected between the vertical arm and the other swivel connection which results in a counterbalance effect on the vertical arm to prevent the central head assembly from dropping downwardly when the universal joints are unlocked.

19. A system of claim 15, wherein the two universal joints are mounted in a housing portion of the central head assembly such that the universal joints are substantially opposed.

20. A system of claim 19, wherein the universal joint locking means includes a linkage assembly and two pusher members, the pusher members contacting a portion of the respective universal joints, tending to force them outwardly against a portion of the central head assembly housing portion in which the universal joints are mounted, locking the universal joints in place.

21. A system of claim 20, wherein the universal joint locking means further includes a push rod which is urged against the linkage assembly so as to force the pusher members outwardly, the locking means including a main spring which acts against a first portion of the push rod, urging the push rod against the linkage assembly.

22. A system of claim 20, including a second spring acting on a second portion of the push rod tending to force it against the linkage assembly, wherein the pressure of the second spring provides a small amount of pressure on the universal joints, requiring some effort on the part of the operator to move the universal joints with the handle, such that the central head assembly generally remains in position when the two universal joints are unlocked.

23. An adjustable mounting apparatus, comprising:

two spaced-apart swivel assemblies, each swivel assembly including at least one swivel connection permitting movement of a portion of the swivel assembly in a horizontal plane and at least one other swivel connection permitting movement of a portion of the swivel assembly in a vertical plane, and further including means for locking the swivel connections;

a central head assembly, which includes two universal joints, the central head assembly further including means for locking the universal joints and means connecting the two universal joints, respectively, to the two swivel assemblies; and handle means extending from the central head assembly which includes means for unlocking the two universal joints substantially simultaneously with a single action, to permit movement of the central head assembly.

24. A system of claim 23, including clamping members locking each of the swivel assemblies to a table.

25. A system of claim 24, wherein each swivel assembly includes a support rod which is fixedly connected to the clamping member and extends therefrom to the one swivel connection, a first swivel rod which extends from the first swivel connection to a thud swivel connection and a second swivel rod which extends from the third swivel connection to the other swivel connection, wherein the first and second swivel rods rotate in the horizontal plane about the one and third swivel connections, each swivel assembly, respectively, further including a vertical arm which extends between the other swivel connection and one of the universal joint in the central head assembly, wherein the vertical arm swivels in a vertical plane about the other swivel connection, wherein the other and third swivel connections include means for locking the vertical arm and the first and second swivel arms in place.

26. A system of claim 25, including a spring element connected between the vertical arm and the other swivel connection which results in a counterbalance effect on the vertical arm to prevent the central head assembly from dropping downwardly when the universal joints are unlocked.

27. A system of claim 23, wherein the two universal joints are mounted in a housing portion of the central head assembly such that the universal joints are substantially opposed.

28. A system of claim 27, wherein the universal joint locking means includes a linkage assembly and two pusher members, the pusher members contacting a portion of the respective universal joints, tending to force them outwardly against a portion of the central head assembly housing portion, locking the universal joints in place.

29. A system of claim 28, wherein the universal joint locking means further include a push rod which is urged against the linkage assembly so as to force the pusher members outwardly, the locking means including a main spring which acts against a first portion of the push rod, urging the push rod against the linkage assembly.

30. A system of claim 28, including a second spring acting on a second portion of the push rod tending to force it against the linkage assembly, wherein the pressure of the second spring provides a small amount of pressure on the universal joints, requiring some effort on the part of the operator to move the universal joints with the handle, such that the central head assembly generally remains in position when the two universal joints are unlocked.

* * * * *